(12) United States Patent
Taghiyari et al.

(10) Patent No.: US 8,079,249 B2
(45) Date of Patent: Dec. 20, 2011

(54) GAS PERMEABILITY MEASUREMENT APPARATUS

(76) Inventors: Hamid Reza Taghiyari, Tehran (IR); Ali Naghi Karimi, Tehran (IR); Davood Parsapajouh, Tehran (IR)

( * ) Notice: Subject to any disclaimer, the term of this patent is extended or adjusted under 35 U.S.C. 154(b) by 461 days.

(21) Appl. No.: 12/436,812

(22) Filed: May 7, 2009

(65) Prior Publication Data
US 2010/0281951 A1    Nov. 11, 2010

(51) Int. Cl.
*G01N 15/08* (2006.01)
(52) U.S. Cl. .......................................................... 73/38
(58) Field of Classification Search .................. None
See application file for complete search history.

*Primary Examiner* — Hezron E Williams
*Assistant Examiner* — Alex Devito

(74) *Attorney, Agent, or Firm* — Barry Choobin; Choobin & Choobin Consultancy LLC

(57) ABSTRACT

Gas permeability measurement apparatus is an apparatus for measuring all kinds of continuous-porous materials, including wood, paper, wood-composites, wood plastic composites (WPC), minerals, polymer-based materials, minerals, ceramics, textiles and fabrics. The apparatus is equipped with an electronic time measurement device with milli-second precision; this feature allows the permeability values to have improved accuracy and precision needed for scientific purposes. This apparatus uses falling liquid method wherein the liquid column can be easily changed according to test design. The apparatus is equipped with at least two sensors in the electronic time measurement device which are designed so that the distance between them can be easily set to 10, 15, and 20 cm. The sensors are mounted on a stand that can be moved along the liquid and gas traveling zone thereby enabling the length of liquid column to be fixed from 30 cm up to 2 meters. The main skeleton of the whole apparatus is designed so that the diameter of its glass tube may easily be changed from 0.5 to 5 cm in accordance to different standard stipulations, as well as the amount of liquid displacement required.

14 Claims, 2 Drawing Sheets

GAS PERMEABILITY MEASUREMENT APPARATUS

SPONSORSHIP STATEMENT

The present invention is sponsored by Iranian National Science foundation and Shahid Rajaee Teacher Training University.

FIELD OF THE INVENTION

The present invention relates to processes and apparatus for making a measurement of any kind or for making a test of any kind, and takes all such subject matter. In particular the present invention relates to Subject matter for determining through the direct application of fluid under pressure the porosity (i.e., volume of interstices) of solids, the fineness of powdered materials, or action of filters; also, the determining of permeability (i.e., the passage or diffusibility of fluids through a specimen).

BACKGROUND OF THE INVENTION

In programs of special analysis of rock samples or core samples taken from a medium, such as an underground region, establishment of initial representative water saturation plays a key role in core sample preparation. The point is to establish fluids in proportions representative of those originally present in the reservoir region after migration of the oil. Typically, if the effectiveness of water injection is to be studied and the capillary pressure curve and relative permeability curve are to be measured, the initial saturation Swi is important and must be representative of the in-situ conditions. The term "initial" is used advisedly here to avoid any confusion with the term "irreducible" which describes the asymptotic saturation obtained with a high capillary pressure for a given set of fluids. In a transition zone, these two saturations are very different.

According to a standard procedure, the samples are extracted from full-diameter core samples, and then cleaned with appropriate solvents. The samples are then brought to initial saturation (Swi) or irreducible saturation (Swirr) depending on their position in terms of capillary pressure, and aged with crude oil. At this stage, the amount of water present also plays a decisive role in obtaining a representative state of wettability. This is why a substantial effort is generally made to establish this initial saturation (Swi).

Several known techniques enable this condition to be reached. For example, the water-saturated sample can be confined in a cell and this water can be displaced by injecting oil. It is known, however, that it is difficult to obtain low water saturations, essentially because of the presence of heterogeneities despite the use of viscous oil (typically 50 cP). Viscous oil can also be somewhat impractical for low permeabilities. The average saturation can hence still be high after breakthrough and residual production can be significant and take several days. Moreover, the saturation profile is highly non-uniform, as is the case with standard centrifugation. This profile can however be reduced by reversing the injection direction. Although centrifugation is the most effective technique for saturating core samples, it cannot be used to establish saturation (Swi) because of the presence of a high saturation profile which can give rise to interpretation problems in later injection experiments. For example, one may cite the substitution technique, the drainage method for which the main difficulty is controlling or imposing the salinity and the saturation profile. The ideal would be to use a capillarity displacement process, as is the case in situ, with an experimental time compatible with the schedule of the development or evaluation program, which is generally short. To avoid non-uniform profiles and obtain low water saturation, the porous plate method can be used instead of the above-mentioned techniques. The experiments are time-consuming, taking a few weeks to a few months, particularly in the case of long core samples. Moreover, the capillary contact between the core sample and the porous plate is often difficult to optimize and may lead to a low success rate.

The centrifugation technique is probably the most attractive solution. This is a displacement process dominated by capillarity, which is rapid and inexpensive and has a number of practical advantages. Its main drawback is however the non-uniformity of the saturation profile and, for certain centrifuges, the limit imposed by the length of the core samples.

Furthermore, gas permeability measuring apparatuses are generally known in the prior art. Such apparatuses typically include one or more sensing heads which are adapted for holding a membrane material across a chamber, wherein a gas such as oxygen may be admitted into the chamber on one side of the membrane, and a detector such as an oxygen detector may be coupled via passages to the other side of the chamber, to measure the amount of oxygen which passes through the membrane. Since all membranes are permeable to some extent, it is usually possible to detect a measurable amount of oxygen passing through the membrane over a finite period of time. In the prior art, gas permeability measuring apparatuses utilized one or more of such measuring heads coupled via hoses and tubing to sensors and the like, to perform fairly accurate measurements of membrane permeability.

Measurement of gas permeability through membranes requires extremely sensitive gas detectors or sensors, for the quantities of measured gas are frequently quite low. It is therefore extremely important that the entire system involved in such measurements be maintained under tightly sealed conditions, particularly with respect to all of the gas flow passages leading to the gas detector. Prior art permeability measuring instruments typically utilize hoses or tubing to interconnect the necessary instrumentation, wherein each of the connecting junctions is susceptible to leakage.

Therefore, it would be advantageous to provide a permeability measurement apparatus and method to overcome the above short comings.

SUMMARY OF THE INVENTION

According to preferred embodiment, the principal object of the invention is to provide a gas permeability apparatus for measuring gas permeability through a membrane.

Yet another object of the present invention is to provide an improved gas permeability measuring apparatus which permits such measurements to be accomplished at substantially constant temperature and relative humidity with high precision by a time measuring device which has precision in millisecond.

Yet another object of the present invention is to provide an improved gas permeability measuring apparatus having improved time measurement system over prior art.

Yet another object of the present invention is to provide a gas permeability measurement apparatus capable of introducing distance measurement between at least two sensors which are placed in the apparatus.

Yet another object of the present invention is to provide a gas permeability measurement apparatus capable of measuring gas permeability based on traveling time of liquid in the system.

Yet another object of the present invention is to provide a gas permeability apparatus capable of introducing a plurality of sensors to measure the traveling time of liquid in the system.

Yet another object of the present invention is to provide a gas permeability apparatus capable of introducing a time measuring device to measure in milli-second the traveling time of liquid in the system.

Yet another object of the present invention is to provide a gas permeability apparatus capable of introducing a holder to hold different specimen with different sizes.

Yet another object of the present invention is to provide a gas permeability apparatus capable of introducing a holder to hold different specimen with different shapes.

Yet another object of the present invention is to provide a gas permeability apparatus capable of introducing a system to use different gases.

Yet another object of the present invention is to provide a gas permeability apparatus capable of introducing a system to use different liquid with different viscosity and density.

Yet another object of the present invention is to provide a gas permeability apparatus capable of introducing a system to measure gas permeability values for textiles and fabrics.

Yet another object of the present invention is to provide a method for Gas Permeability Measurement of a target porous specimen comprising steps of:
 Supplying a first predetermined amount of liquid in a first container;
 Supplying and storing a second predetermined amount of liquid to a second container, wherein the surface level of said second predetermined amount of liquid reaches a predetermined level in said second container;
 Discharging excessive amount of liquid above said predetermined level in said second container by connecting a drainage pipe to said second container;
 Releasing a third predetermined amount of liquid from said first container to a liquid and gas traveling zone wherein said liquid and gas traveling zone comprises of a first end and a second end, and at least a first sensor and a second sensor which are mounted on a stand attached to said liquid and gas traveling zone, and wherein said second end is immersed in said second predetermined amount of liquid in said second container, and wherein said second end of said liquid and gas traveling zone is sealed to maintain said third predetermined amount of liquid in said liquid and gas traveling zone at a first level in said liquid and gas traveling zone, and wherein said first level in said liquid and gas traveling zone is above said at least first and second sensors;
 Placing said target porous specimen at said first end of said liquid and gas traveling zone;
 Measuring a traveling time of said third predetermined amount of liquid in said liquid and gas traveling zone between said at least first sensor and second sensor by unsealing said second end of said liquid and gas traveling zone;
 Calculating a gas permeability value for said target porous specimen based on said a traveling time according to:

$$k_g = \frac{V_d CL(P_{atm} - 0.074 \times \bar{z})}{tA(0.074 \times \bar{z})(P_{atm} - 0.037 \times \bar{z})} \times \frac{0.760 \text{ mHg}}{1.013 \times 10^6 \text{ Pa}}$$

$$C = 1 + \frac{V_r(0.074 \times \Delta z)}{V_d(P_{atm} - 0.074\bar{z})}$$

Where:
 $k_g$=longitudinal specific permeability (m$^3$/m);
 $V_d$=$\pi r^2 \Delta z$ [r=radius of liquid and gas traveling zone (m)] (m$^3$);
 C=correction factor for gas expansion as a result of change in static head and viscosity of liquid;
 L=length of target porous specimen (m);
 $P_{atm}$=atmospheric pressure (mHg);
 $\bar{z}$=average height of liquid level in said liquid and gas traveling zone between said at least first sensor and second sensor during time of measurement (m);
 t=time (s);
 A=cross-sectional area of target porous specimen (m$^2$);
 $\Delta z$=change in height of liquid during time t (m);
 $V_r$=volume between first sensor and first end of the liquid and gas traveling zone (m$^3$).

Yet another object of the present invention is to provide a method for Gas Permeability Measurement of a target porous specimen wherein said target porous specimen comprises of wood (longitudinal, tangential, and radial directions), paper, wood-composites, wood plastic composites (WPC), polymer-based materials, minerals and ceramics.

Yet another object of the present invention is to provide a method for Gas Permeability Measurement of a target porous specimen wherein said plurality sensors are adjustable.

Yet another object of the present invention is to provide a method for Gas Permeability Measurement of a target porous specimen wherein said at least first and second sensor are placed on an adjustable base and wherein said adjustable base is in vicinity of said liquid and gas traveling zone.

Yet another object of the present invention is to provide an apparatus for gas permeability measurement of a target porous specimen comprising:
 Means for supplying a first predetermined amount of liquid in a first container;
 Means for supplying and storing a second predetermined amount of liquid to a second container, wherein the surface level of said second predetermined amount of liquid reaches a predetermined level in said second container;
 Means for discharging excessive amount of liquid above said predetermined level in said second container by connecting drainage pipe to said second container;
 Means for releasing a third predetermined amount of liquid from said first container to a liquid and gas traveling zone wherein said liquid and gas traveling zone comprises of a first end and a second end, and at least a first sensor and a second sensor which are mounted on a stand attached to said liquid and gas traveling zone, and wherein said second end is immersed in said second predetermined amount of liquid in said second container, and wherein said second end of said liquid and gas traveling zone is sealed to maintain said third predetermined amount of liquid in said liquid and gas traveling zone at a first level in said liquid and gas traveling zone, and wherein said first level in said liquid and gas traveling zone is above said at least first and second sensors;
 Means for placing said target porous specimen at said first end of said liquid and gas traveling zone;
 Means for measuring a traveling time of said third predetermined amount of liquid traveling between said at least first sensor and second sensor by unsealing said second end of said liquid and gas traveling zone;
 Means for calculating a gas permeability value for said target porous specimen based on said a traveling time according to:

$$k_g = \frac{V_d CL(P_{atm} - 0.074 \times \bar{z})}{tA(0.074 \times \bar{z})(P_{atm} - 0.037 \times \bar{z})} \times \frac{0.760 \text{ mHg}}{1.013 \times 10^6 \text{ Pa}}$$

$$C = 1 + \frac{V_r(0.074 \times \Delta z)}{V_d(P_{atm} - 0.074\bar{z})}$$

Where:
$k_g$=longitudinal specific permeability (m³/m);
$V_d = \pi r^2 \Delta z$ [r=radius of liquid and gas traveling zone (m)] (m³);
C=correction factor for gas expansion as a result of change in static head and viscosity of liquid;
L=length of target porous specimen (m);
$P_{atm}$=atmospheric pressure (mHg);
$\bar{z}$=average height of liquid level in said liquid and gas traveling zone between said at least first sensor and second sensor during time of measurement (m);
t=time (s);
A=cross-sectional area of target porous specimen (m²);
$\Delta z$=change in height of liquid during time t (m);
$V_r$=volume between first sensor and first end of the liquid and gas traveling zone (m³).

Yet another object of the present invention is to provide an apparatus for gas permeability measurement of a target porous specimen wherein said means for measuring said traveling time functions with milli-second precision.

Yet another object of the present invention is to provide an apparatus for gas permeability measurement of a target porous specimen wherein means for measuring said traveling time comprises a plurality of sensors for sensing said traveling time.

Yet another object of the present invention is to provide an apparatus for gas permeability measurement of a target porous specimen wherein said target porous specimen comprises of wood (longitudinal, tangential, and radial directions), paper, wood-composites, wood plastic composites (WPC), polymer-based materials, minerals and ceramics.

Yet another object of the present invention is to provide an apparatus for gas permeability measurement of a target porous specimen wherein said plurality sensors are adjustable.

Yet another object of the present invention is to provide an apparatus for gas permeability measurement of a target porous specimen wherein said plurality of sensors are placed on an adjustable base and wherein said adjustable base is in vicinity of said liquid and gas traveling zone.

Yet another object of the present invention is to provide an apparatus for gas permeability measurement of a target porous specimen wherein said apparatus is equipped with a drainage pipe to stabilize said second predetermined amount of liquid.

Yet another object of the present invention is to provide an apparatus for gas permeability measurement of a target porous specimen wherein said first container employs gravity to fill said third predetermined amount of liquid in said liquid and gas traveling zone.

Yet another object of the present invention is to provide an apparatus for gas permeability measurement of a target porous specimen wherein said apparatus further comprises:
A plurality of time measurement devices for measuring gas permeability of said target porous specimen in multiple elevations;
Means for comparing measurements in said multiple stages.

Yet another object of the present invention is to provide an apparatus for gas permeability measurement of a target porous specimen wherein said apparatus further comprises: Means for holding said target porous specimen wherein said target porous specimen comprises variable shapes and variable sizes.

The forgoing and other objects and advantages of the present invention will be apparent from the following specification and claims, and with reference to the appended drawings.

DETAILED DESCRIPTION OF THE INVENTION

Figure 2:
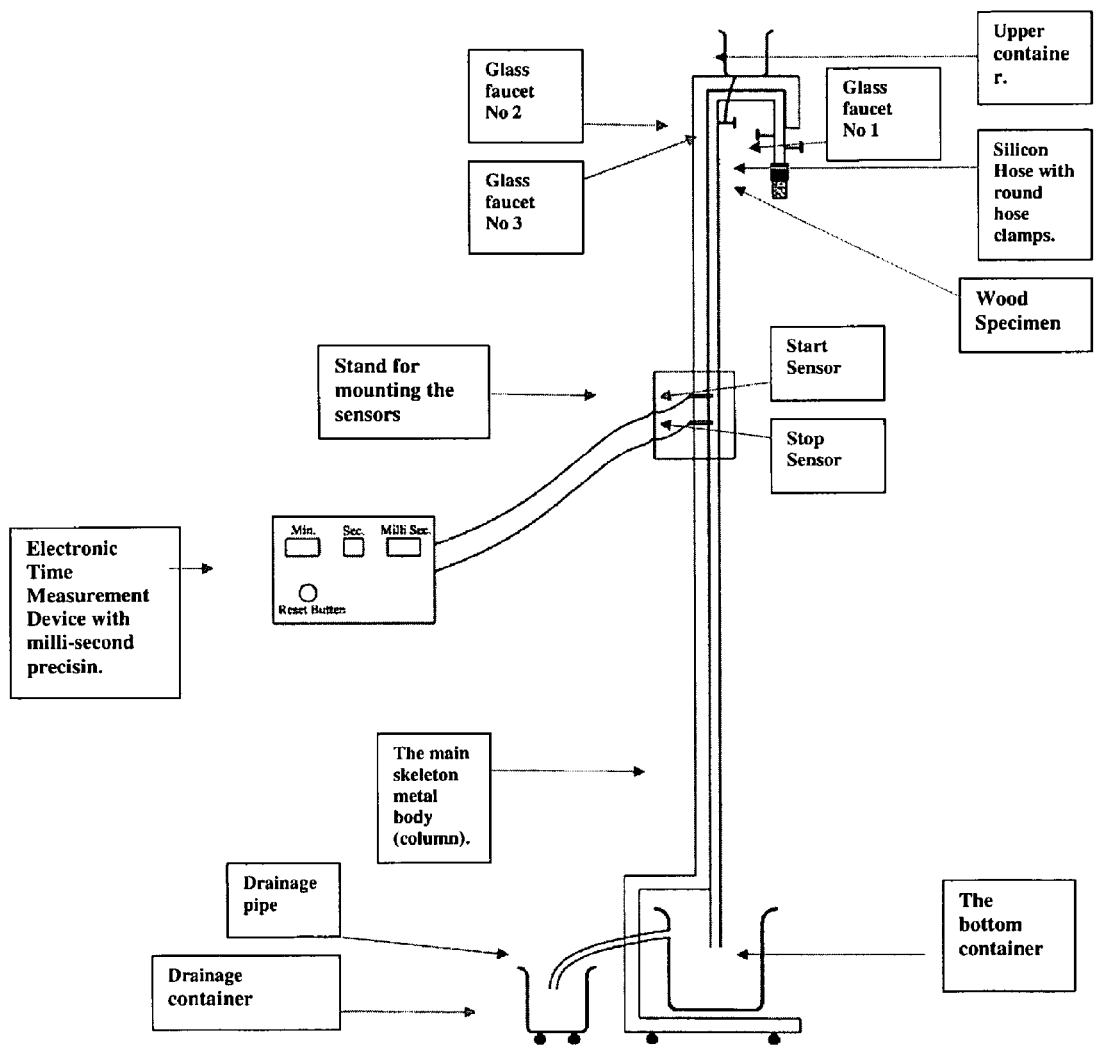
FIG. 2 shows the overview of the Gas Permeability Apparatus with Electronic Time Measurement Device according to the present invention.

The present invention has delicate capabilities of measuring permeability of porous materials with precision required for scientific purposes. The present invention is equipped with electronic time measurement device, it is to be noted that time measurement plays a vital role in permeability measurement due to the fact that the time which takes for the liquid column to travel from a first sensor to a second sensor as shown in FIG. 2 would be put in an equation to determine permeability value. In this connection, sometimes the difference between specimens are so little that prevents the accuracy of naked eye to measure the exact time; also, in very permeable materials, sometimes the time itself is under one single second, therefore, the essential need for an exact time measurement device would be crystal clear. The present invention provides a permeability measurement apparatus which is equipped with a time measurement device, and its accuracy is high (milli-second precision) that satisfy all scientific needs. In the meantime, connection of the time measurement device to the main apparatus is through electric wire and in a way that reading the time could be done in a far distance from the main skeleton body. This could make the usage of the apparatus quite easy in places (chambers) where the presence of operator is not possible or hazardous due to toxic gases.

The present invention employs gravity to fill in the liquid and gas traveling zone with liquid whereas the prior art employs vacuum pump. This makes the apparatus able to be used in places there is no electricity, or in places electricity is hazardous.

The present invention provides a gas permeability apparatus that has liquid and gas traveling zone as thin as 5 mm in diameter. The thinner the diameter is the more accuracy and precision will be achieved because the volume of liquid displaced would be less and could be measure with higher precision.

The present invention provides a gas permeability apparatus which permitted liquid column to be 2 meter high. Sometimes, the permeability of the material we are working on is very low. In these circumstances, the high liquid column is very useful as to the fact that it provides enough vacuum pressure for the gas to pass through the porous specimen.

In one embodiment, the present invention provides a gas permeability apparatus comprising a bottom container which is equipped with drainage pipe to keep the liquid level in the liquid container constant. The vacuum pressure is procured through the liquid column, and therefore, the height plays a delicate role in this connection. Naturally, the basic permeability values obtained may be used for different purposes. The high precision of time measuring device (having precision in milli-second) that is included in the apparatus makes it reliable for scientific uses. In the meantime, user-friendly procedures as well as not very expensive price make it favorable for industrial applications.

The above and other needs are met by the present invention which, in one embodiment, provides a method for measuring gas permeability of all kinds of continuous-porous materials, including wood (longitudinal, tangential, and radial directions), paper, wood-composites, wood plastic composites (WPO), polymer-based materials, etc.

In another embodiment the present invention provides a system comprising: a round sample with known length as well as known cross-section area in which prepared to be placed in the holder of the apparatus and be tightly tide up with silicon hose and round hose clamps. Other shapes in cross-section may also be used with this apparatus, based on the shape of the holder. Then, glass faucet (tap) No 1 is turned open, a rubber cap is placed in the end of liquid and gas traveling zone to prevent liquid passing. Glass faucet No 2 is turned open to let liquid pass from the upper liquid container and fill liquid column to at least 20 cm above first sensor or the start sensor.

While the liquid column is ready in the liquid and gas traveling zone, glass faucet No 1 as well as glass faucet No 2 are closed. The seal is then removed slowly so that fluctuations in the surface of liquid column would be the least. The reset button on electronic measuring time device is pushed to reset the device to zero. When the surface level of liquid column is still, glass faucet No 1 is turned wide open to let the liquid pass through the sample. When the liquid column reached the start sensor it makes electronic time measurement device to start running; and when it reaches second sensor or stop sensor, the time on the electronic device would automatically stops. The time measured wouldn't disappear until the reset button in pushed again, that is, there is enough time to write down the time measured. The falling liquid from liquid and gas traveling zone will be collected in the bottom container. The bottom liquid container is designed so that the surface level of liquid is always the same and extra liquid falling from liquid column would automatically drain from the bottom container through the drainage pipe. Glass faucet No. 3 is used when repeating measurement of a single specimen; when the permeability of the specimen fixed to the holder is very low, the liquid column cannot be filled in simply by turning on faucets No. 1 and 2 because the air displaced by liquid that fills the liquid column should go out of the liquid and gas traveling zone, but due to slow passing of air through the specimen it is not possible. Therefore, faucet No. 3 would be turned open to let air displacement easy.

Figure 1:
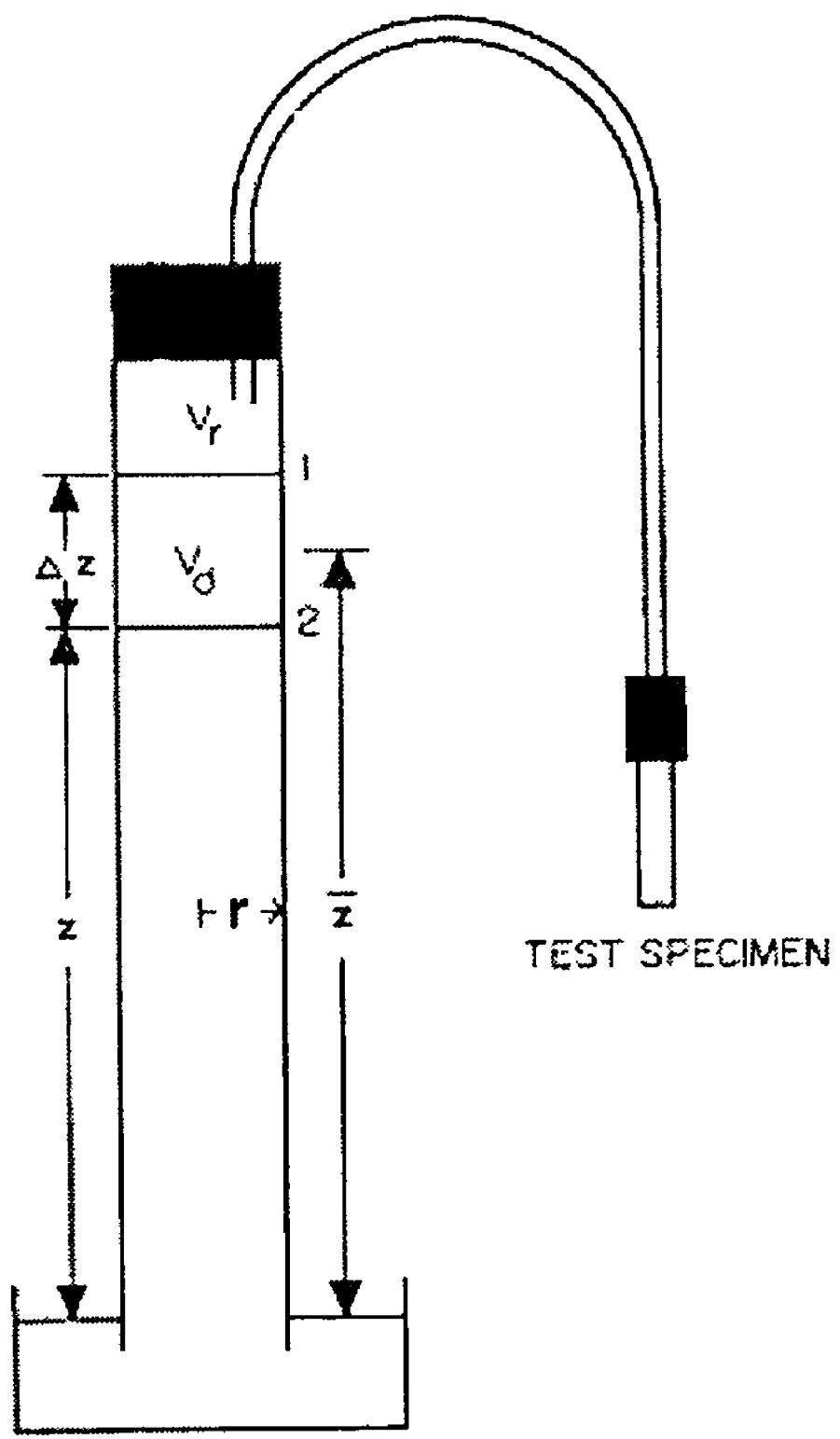
FIG. 1 shows a schematic drawing of the Gas Permeability Measurement Apparatus according to the present invention.

Once the time is measured, permeability values would be determined using following equations (a simple schematic drawing of the apparatus is shown in FIG. 1 for better understanding of the procedure of the working method):

$$k_g = \frac{V_d C L (P_{atm} - 0.074 \times \bar{z})}{tA(0.074 \times \bar{z})(P_{atm} - 0.037 \times \bar{z})} \times \frac{0.760 \text{ mHg}}{1.013 \times 10^6 \text{ Pa}} \quad \text{(Formula 1)}$$

$$C = 1 + \frac{V_r(0.074 \times \Delta z)}{V_d(P_{atm} - 0.074\bar{z})} \quad \text{(Formula 2)}$$

Where:
$k_g$=longitudinal specific permeability (m$^3$/m);
$V_d = \pi r^2 \Delta z$ [r=radius of liquid and gas traveling zone (m)] (m$^3$);
C=correction factor for gas expansion as a result of change in static head and viscosity of liquid;

L=length of target porous specimen (m);
$P_{atm}$=atmospheric pressure (mHg);
$\bar{z}$=average height of liquid level in said liquid and gas traveling zone between said at least first sensor and second sensor during time of measurement (m);
t=time (s);
A=cross-sectional area of target porous specimen (m$^2$);
$\Delta z$=change in height of liquid during time t (m);
$V_r$=volume between first sensor and first end of the liquid and gas traveling zone (m$^3$).

The calculated superficial permeability coefficients are then multiplied by the viscosity of the gas (if the gas is air, the viscosity would be: $\mu$=1.81×10−5 Pa s) for the calculation of their specific permeability (K=kg·$\mu$) which is independent of the measuring gas and solely a function of the material itself.

The stand for sensors is designed so that the distance between them can easily be put to 10, 15, and 20 cm.

Different diameter of liquid and gas traveling zone can be easily used in the apparatus. The diameter of liquid and gas traveling zone may be from 0.5 cm up to 5 cm.

Permeability may be measured with different liquid column heights from full 2 m to 30 cm; it is to be noted that liquid columns less than 30 cm wouldn't be practical in tight-grained porous materials. Sensor stand is designed so that its place can be easily changed between the above mentioned span. Furthermore, it is possible to fix 2 or more stands connected to 2 or more time measurement devices at a time in order to measure falling time of different liquid column heights and compare them together.

The bottom liquid container is equipped with a drainage pipe so that the liquid surface in the bottom container would always be the same. This would guarantee that the liquid column wouldn't change in height.

As to the fact that permeability, in many materials, is related to the moisture content of the material (especially in hygroscopic materials such as wood and paper), it is recommended to first condition the specimens in a conditioning chamber. Also, it is recommended to monitor the relative humidity of the gas used. This way, all specimens in different runs and different times would have the same moisture content.

It is recommended to measure the time for each single specimen three times, and an average of three times being calculated for each specimen.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

We claim:

1. A method for Gas Permeability Measurement of a target porous specimen comprising steps of:

Supplying a first predetermined amount of liquid in a first container;

Supplying and storing a second predetermined amount of liquid to a second container, wherein the surface level of said second predetermined amount of liquid reaches a predetermined level in said second container;

Discharging excessive amount of liquid above said predetermined level in said second container by connecting a drainage pipe to said second container;

Releasing a third predetermined amount of liquid from said first container to a liquid and gas traveling zone wherein said liquid and gas traveling zone comprises of a first end and a second end, and at least a first sensor and a second sensor which are mounted on a stand attached to said liquid and gas traveling zone, and wherein said second end is immersed in said second predetermined amount of liquid in said second container, and wherein said second end of said liquid and gas traveling zone is sealed to maintain said third predetermined amount of liquid in said liquid and gas traveling zone at a first level in said liquid and gas traveling zone, and wherein said first level in said liquid and gas traveling zone is above said at least first and second sensors;

Placing said target porous specimen at said first end of said liquid and gas traveling zone;

Measuring a traveling time of said third predetermined amount of liquid traveling between said at least first sensor and second sensor by unsealing said second end of said liquid and gas traveling zone;

Calculating a gas permeability value for said target porous specimen based on said a traveling time according to:

$$k_g = \frac{V_d C L (P_{atm} - 0.074 \times \bar{z})}{tA(0.074 \times \bar{z})(P_{atm} - 0.037 \times \bar{z})} \times \frac{0.760 \text{ mHg}}{1.013 \times 10^6 \text{ Pa}}$$

$$C = 1 + \frac{V_r(0.074 \times \Delta z)}{V_d(P_{atm} - 0.074\bar{z})}$$

Where:
$k_g$=longitudinal specific permeability (m³/m);
$V_d = \pi r^2 \Delta z$ [r=radius of liquid and gas traveling zone (m)] (m³);
C=correction factor for gas expansion as a result of change in static head and viscosity of liquid;
L=length of target porous specimen (m);
$P_{atm}$=atmospheric pressure (mHg);
$\bar{z}$=average height of liquid level in said liquid and gas traveling zone between said at least first sensor and second sensor during time of measurement (m);
t=time (s);
A=cross-sectional area of target porous specimen (m²);
$\Delta z$=change in height of liquid during time t (m);
$V_r$=volume between first sensor and first end of the liquid and gas traveling zone (m³).

2. The method as claimed in claim 1, wherein said target porous specimen comprises of wood (longitudinal, tangential, and radial directions), paper, wood-composites, wood plastic composites (WPC), polymer-based materials, minerals and ceramics.

3. The method as claimed in claim 1, wherein said plurality sensors are adjustable.

4. The method as claimed in claim 1, wherein said at least first and second sensor are placed on an adjustable base and wherein said adjustable base is in vicinity of said liquid and gas traveling zone.

5. An apparatus for gas permeability measurement of a target porous specimen comprising:
Means for supplying a first predetermined amount of liquid in a first container;
Means for supplying and storing a second predetermined amount of liquid to a second container, wherein the surface level of said second predetermined amount of liquid reaches a predetermined level in said second container;
Means for discharging excessive amount of liquid above said predetermined level in said second container by connecting drainage pipe to said second container;
Means for releasing a third predetermined amount of liquid from said first container to a liquid and gas traveling zone wherein said liquid and gas traveling zone comprises of a first end and a second end, and at least a first sensor and a second sensor which are mounted on a stand attached to said liquid and gas traveling zone, and wherein said second end is immersed in said second predetermined amount of liquid in said second container, and wherein said second end of said liquid and gas traveling zone is sealed to maintain said third predetermined amount of liquid in said liquid and gas traveling zone at a first level in said liquid and gas traveling zone, and wherein said first level in said liquid and gas traveling zone is above said at least first and second sensors;

Means for placing said target porous specimen at said first end of said liquid and gas traveling zone;

Means for measuring a traveling time of said third predetermined amount of liquid traveling between said at least first sensor and second sensor by unsealing said second end of said liquid and gas traveling zone;

Means for calculating a gas permeability value for said target porous specimen based on said a traveling time according to:

$$k_g = \frac{V_d C L (P_{atm} - 0.074 \times \bar{z})}{tA(0.074 \times \bar{z})(P_{atm} - 0.037 \times \bar{z})} \times \frac{0.760 \text{ mHg}}{1.013 \times 10^6 \text{ Pa}}$$

$$C = 1 + \frac{V_r(0.074 \times \Delta z)}{V_d(P_{atm} - 0.074\bar{z})}$$

Where:
$k_g$=longitudinal specific permeability (m³/m);
$V_d = \pi r^2 \Delta z$ [r=radius of liquid and gas traveling zone (m)] (m³);
C=correction factor for gas expansion as a result of change in static head and viscosity of liquid;
L=length of target porous specimen (m);
$P_{atm}$=atmospheric pressure (mHg);
$\bar{z}$=average height of liquid level in said liquid and gas traveling zone between said at least first sensor and second sensor during time of measurement (m);
t=time (s);
A=cross-sectional area of target porous specimen (m²);
$\Delta z$=change in height of liquid during time t (m);
$V_r$=volume between first sensor and first end of the liquid and gas traveling zone (m³).

6. The apparatus as claimed in claim 5, wherein said means for measuring said traveling time functions with milli-second precision.

7. The apparatus as claimed in claim 5, wherein said means for measuring said traveling time comprises a plurality of sensors for sensing said traveling time.

8. The apparatus as claimed in claim 5, wherein said target porous specimen comprises of wood (longitudinal, tangential, and radial directions), paper, wood-composites, wood plastic composites (WPC), polymer-based materials, minerals and ceramics.

9. The apparatus as claimed in claim 5, wherein said plurality sensors are adjustable.

10. The apparatus as claimed in claim 5, wherein said plurality of sensors are placed on an adjustable base and wherein said adjustable base is in vicinity of said liquid and gas traveling zone.

11. The apparatus as claimed in claim 5, wherein said apparatus is equipped with a drainage pipe to stabilize said second predetermined amount of liquid.

12. The apparatus as claimed in claim 5, wherein said first container employs gravity to fill said third predetermined amount of liquid in said liquid and gas traveling zone.

13. The apparatus as claimed in claim 5, wherein said apparatus further comprises:

A plurality of time measurement devices for measuring gas permeability of said target porous specimen in multiple stages;

Means for comparing measurements in said multiple stages.

14. The apparatus as claimed in claim 5, wherein said apparatus further comprises:

Means for holding said target porous specimen wherein said target porous specimen comprises variable shapes and variable sizes.

\* \* \* \* \*